(12) United States Patent
Howell et al.

(10) Patent No.: US 7,518,123 B2
(45) Date of Patent: Apr. 14, 2009

(54) HEAT CAPACITOR FOR CAPILLARY AEROSOL GENERATOR

(75) Inventors: Tony Howell, Midlothian, VA (US);
Clover Hariaczyi, Glen Allen, VA (US);
Marc Belcastro, Glen Allen, VA (US)

(73) Assignee: Philip Morris USA Inc., Richmond, VA (US)

( * ) Notice: Subject to any disclaimer, the term of this patent is extended or adjusted under 35 U.S.C. 154(b) by 247 days.

(21) Appl. No.: 11/526,123

(22) Filed: Sep. 25, 2006

(65) Prior Publication Data

US 2008/0073558 A1   Mar. 27, 2008

(51) Int. Cl.
*A61M 16/00* (2006.01)
*F24J 3/00* (2006.01)
*A62B 7/00* (2006.01)
*H01J 27/00* (2006.01)

(52) U.S. Cl. .................. 250/425; 250/423 R; 250/424; 250/288; 128/200.14; 128/203.25; 128/203.26; 128/203.27; 128/204.17; 128/204.21; 165/236; 165/104.11; 165/104.17

(58) Field of Classification Search ............... 250/281, 250/282, 288, 423 R, 424, 425; 165/236, 165/104.11, 104.17, 104.19, 104.21, 104.23; 128/200.14, 200.18, 200.19, 203.12, 203.14, 128/203.25, 203.26, 203.27, 204.17, 204.21
See application file for complete search history.

(56) References Cited

U.S. PATENT DOCUMENTS

| 3,299,945 | A | * | 1/1967 | Rice et al. .................. 165/4 |
| 4,755,350 | A | * | 7/1988 | Kennel ....................... 376/321 |
| 5,000,252 | A |   | 3/1991 | Faghri |
| 5,150,832 | A | * | 9/1992 | Degani et al. ............... 228/224 |
| 5,743,251 | A | * | 4/1998 | Howell et al. ............. 128/200.14 |
| 6,089,857 | A | * | 7/2000 | Matsuura et al. ............ 431/142 |
| 6,125,853 | A | * | 10/2000 | Susa et al. .................. 131/273 |
| 6,234,167 | B1 | * | 5/2001 | Cox et al. ................ 128/200.14 |
| 6,570,895 | B2 |   | 5/2003 | Heberle |
| 2002/0144811 | A1 |   | 10/2002 | Chou et al. |
| 2003/0056790 | A1 | * | 3/2003 | Nichols et al. ........ 128/203.16 |

(Continued)

FOREIGN PATENT DOCUMENTS

EP   1867357 A   12/2007

(Continued)

OTHER PUBLICATIONS

FR-1568245TRANS, English Translation of French Patent IDS document FR-1568245, Comstock & Westcott, Inc., 1968, "Respiratory Device for Heat Accumulator".*

(Continued)

*Primary Examiner*—Bernard E Souw
(74) *Attorney, Agent, or Firm*—Buchanan Ingersoll & Rooney PC

(57) ABSTRACT

A heat capacitor for a capillary aerosol generator comprises a phase change material that changes phases at a temperature approximately equal to a temperature sufficient to volatilize liquid material in a capillary passage of the capillary aerosol generator. The phase change material stores heat, which can be used to generate aerosol either continuously or intermittently over a given time. The use of stored heat in the phase change material to generate aerosol over time enables operation of the capillary aerosol generator remote from a large energy source.

19 Claims, 1 Drawing Sheet

U.S. PATENT DOCUMENTS

| | | | | |
|---|---|---|---|---|
| 2003/0106551 A1* | 6/2003 | Sprinkel et al. | ........ | 128/203.16 |
| 2004/0234699 A1* | 11/2004 | Hale et al. | ............... | 427/421.1 |
| 2004/0265519 A1* | 12/2004 | Pellizzari et al. | ........... | 428/34.1 |
| 2005/0079166 A1* | 4/2005 | Damani et al. | .............. | 424/122 |
| 2005/0235991 A1* | 10/2005 | Nichols et al. | ......... | 128/204.17 |
| 2008/0073558 A1* | 3/2008 | Howell et al. | ............... | 250/425 |

FOREIGN PATENT DOCUMENTS

FR      1568245 A      5/1969

OTHER PUBLICATIONS

International Search Report and Written Opinion dated Apr. 15, 2008 for PCT/IB2007/003701.

\* cited by examiner

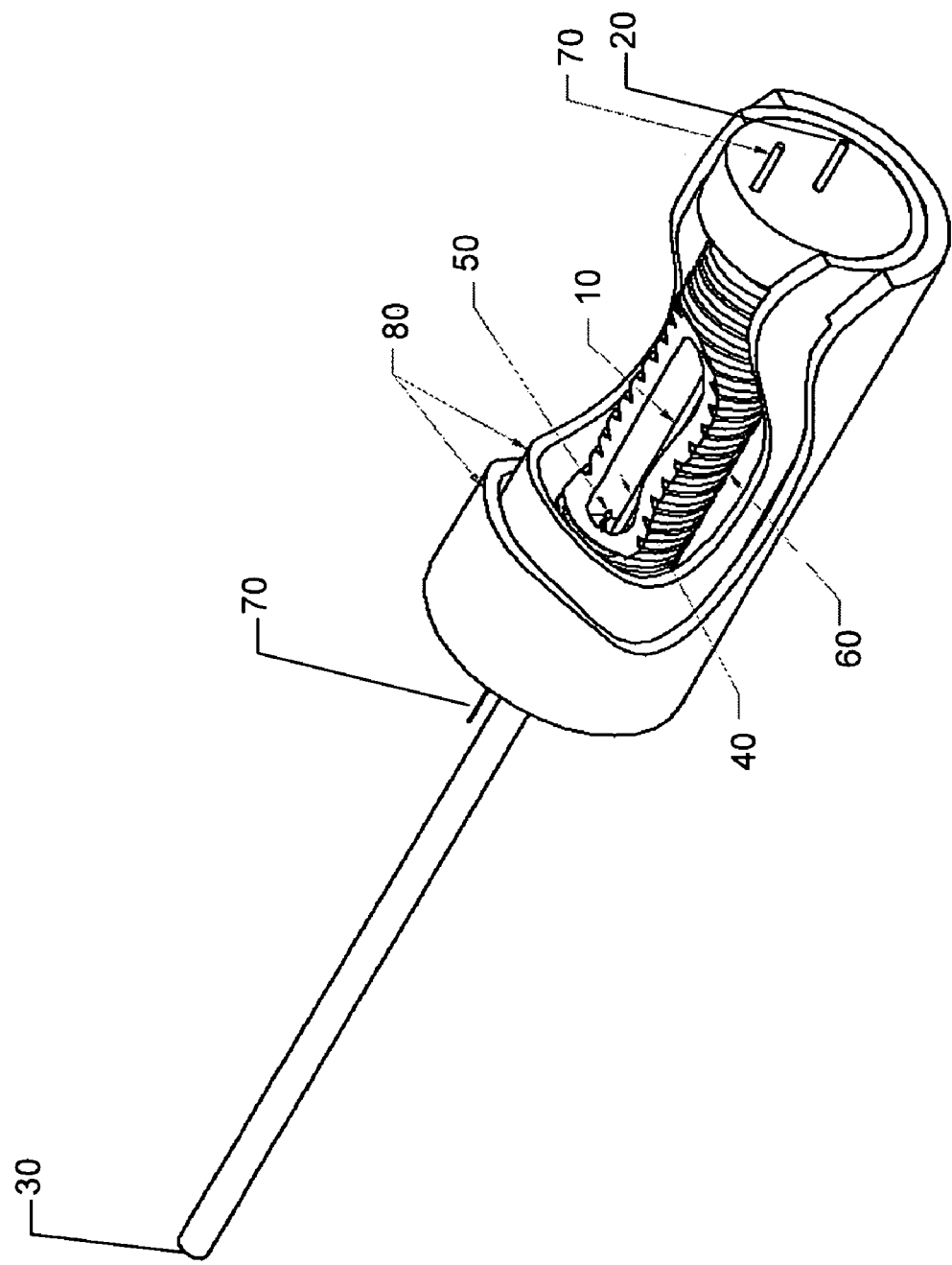
Figure

HEAT CAPACITOR FOR CAPILLARY AEROSOL GENERATOR

SUMMARY

According to one embodiment, a heat capacitor for a capillary aerosol generator comprises a phase change material that changes phases at a temperature approximately equal to a temperature sufficient to volatilize liquid material in a capillary passage of the capillary aerosol generator.

According to another embodiment, a method for generating aerosol uses a capillary aerosol generator comprising the heat capacitor, the method comprising supplying sufficient energy to the phase change material to cause the phase change material to change phases and supplying liquid material to the capillary passage. The phase change material supplies sufficient heat to the liquid material, via the capillary passage, to volatilize liquid material in the capillary passage.

In a further embodiment, a capillary aerosol generator comprises a capillary passage and a heat capacitor comprising a phase change material, which changes phases at a temperature approximately equal to a temperature sufficient to volatilize liquid material in the capillary passage.

BRIEF DESCRIPTION OF THE DRAWING

The FIGURE illustrates a capillary aerosol generator including phase change material, which serves as a heat capacitor.

DETAILED DESCRIPTION OF PREFERRED EMBODIMENTS

A heat capacitor is disclosed herein for use with a capillary aerosol generator wherein the heat capacitor comprises a phase change material. As used herein, the phrase "capillary aerosol generator" refers to capillary aerosol technology, as described in U.S. Pat. No. 5,743,251, the contents of which are hereby incorporated by reference in their entirety. If desired, the capillary can include a constriction at an outlet end as described in U.S. Patent Publication 2005/0235991, the contents of which are hereby incorporated by reference in their entirety.

Specifically, a capillary aerosol generator includes a capillary passage having an inlet and an outlet. A phase change material is positioned adjacent to at least a portion of the capillary passage, but preferably in a way that provides a heated zone around the capillary passage that maximizes heat transfer evenly throughout the heated zone. For example, the phase change material preferably surrounds at least a portion of the capillary passage. The phase change material is preferably contained within a tubular housing. The tubular housing is preferably sized so as to maintain contact between the phase change material, especially the phase change material when it is in a liquid phase, and the capillary passage. The tubular housing is preferably wrapped with heating wire, which may be insulated, and has electrical leads connected to it. The electrical leads are connected to a power supply, preferably a D.C. power supply such as a battery or may be an A.C. power supply such as an electrical socket. Preferred phase change materials include, for example, tin-based solders with various concentrations of tin and/or silver and/or antimony and/or copper and/or bismuth.

While power may be supplied from an electrical socket, the power supply may also be replaceable and rechargeable and may include devices such as a capacitor or, more preferably, a battery. For portable applications, the power supply may be a replaceable, rechargeable battery such as one or more battery cells, e.g., lithium or nickel cadmium battery cells connected in series with a total, non-loaded voltage of approximately 4.8 to 5.6 volts. The characteristics required of the power supply are, however, selected in view of the characteristics of other components of the capillary aerosol generator.

In operation, electrical leads transfer power from the power supply to the heating wire that is wrapped around the tubular housing, thereby heating the phase change material and causing the phase change material to change, for example, from a solid phase to a liquid phase. Thus, the formed liquid phase stores energy, to be released when the liquid phase returns to a solid phase. When heated, the phase change material transfers heat to the portion of the capillary passage and thus heats the portion of the capillary passage to a temperature sufficient to volatilize liquid material that is introduced to the heated capillary passage. The liquid material introduced to the heated capillary passage is volatilized and is driven out of the outlet of the capillary passage. The volatilized material mixes with ambient air outside of the capillary passage to form an aerosol which may or may not be a condensation aerosol.

The heating wire, which may vary depending on the components of the capillary aerosol generator, has such characteristics so as to appropriately heat the tubular housing around which it is wrapped. For example, the heating wire may be insulated and/or have an outside diameter of 0.008 inches, a resistance of 13.1 ohms per foot, and a specific heat of 0.110 BTU/lb-° F. The composition of the heating wire, for example, may be 71.7% iron, 23% chromium, and 5.3% aluminum. Such a heating wire is available from Kanthal Furnace Products, Bethel, Conn.

The capillary passage preferably has an inside diameter of between 0.05 and 0.53 millimeter. A particularly preferred inside diameter of the capillary passage is approximately 0.1 millimeter. While the capillary passage may be comprised of fused silica or aluminum silicate ceramic, other substantially non-reactive materials capable of withstanding repeated heating cycles and generated pressures and having suitable heat conduction properties may also be used. If desired or necessary, an inside wall of the capillary passage may be provided with a coating for reducing the tendency of material to stick to the wall of the capillary passage, which may result in clogging. The capillary passage is preferably comprised of stainless steel or glass.

Liquid material is preferably introduced into the capillary passage through an inlet of the capillary passage connected to a source of liquid material. The volatilized material is driven out of the capillary passage through the outlet of the capillary passage.

In operation, the phase change material is heated to a phase change temperature from an abundant energy source. Thus, the phase change material stores heat (i.e., when a phase change material changes from a solid phase to a liquid phase, heat stored in the liquid phase is released when the liquid phase returns to the solid phase), which is used to generate aerosol over time, for example, greater than about 10 seconds, preferably at least about 1 minute, more preferably about 5 minutes or greater. The use of stored heat in the phase change material to generate aerosol over time enables operation of the capillary aerosol generator remote from a large energy source. A small energy source, for example, a small battery, may be used to supply supplemental energy to the phase change material in order to replenish energy lost or energy used in generating aerosol and preferably maintain the phase change material in a liquid phase. Supplemental energy may be supplied, for example, by pulsing small amounts of electrical energy though the heating wire wrapped around the tubular housing.

The phase change material preferably changes phases at a temperature approximately equal to a temperature sufficient to volatilize liquid material in a capillary passage of the capillary aerosol generator. In particular, as used herein, "approximately equal to" refers preferably to a temperature range of 30° C. greater than a temperature sufficient to volatilize the liquid material to the temperature sufficient to volatilize the liquid material, more preferably to a temperature range of 20° C. greater than the temperature sufficient to volatilize the liquid material to the temperature sufficient to volatilize the liquid material, and even more preferably to a temperature range of 10° C. greater than the temperature sufficient to volatilize the liquid material to the temperature sufficient to volatilize the liquid material.

With reference to the FIGURE, the capillary passage 10 of a capillary aerosol generator has an inlet 30 and outlet 20, as described above. The capillary passage 10 is surrounded by phase change material 40. The temperature of the phase change material 40 may be monitored by use of a thermocouple 50. The phase change material 40 is preferably contained within a tubular, or tubular-like, housing 60. The tubular housing 60 is preferably wrapped in heating wire. Electrical leads 70 are preferably attached to the heating wire. Preferably, the tubular housing 60 is surrounded by insulating sheaths 80.

EXAMPLES

The following examples are provided to be illustrative, but not limiting.

Example 1

As propylene glycol vaporizes/boils at approximately 190° C., a phase change material with a melting point of approximately equal to 230° C. would provide enough energy to aerosolize propylene glycol. Differential scanning calorimetry results from a 98% tin-2% silver alloy reveal a heat of fusion of 55 J/g and a melting point of 221° C. Accordingly, 1.55 g of a 98% tin-2% silver solder is placed in the tubular housing of the FIGURE. The capillary passage is a stainless steel tube. The solder is heated to a temperature of 237° C., as measured by thermocouple, by supplying a power of 16 Watts to the tubular housing though the electrical leads via heating wire. After the solder is maintained at a temperature of 237° C. for 10 seconds, the power to the tubular housing is turned off. A pump supplies propylene glycol to the capillary at a rate of 0.1 mL/minute. Aerosol is generated for 1 minute via stored heat in the solder and not an active heater.

Examples 2-5

A recorded weight of solder is placed in the tubular housing of the FIGURE. The solder is heated above its melting point so that the solder flows uniformly around the capillary and when cooled to solid form remains in intimate contact with the capillary. The solder is heated by passing an electrical current though the heating wire, which is wrapped around the tubular housing. When the temperature of the solder reaches its melting point, the temperature of the solder and thus the stainless steel tube remains fairly constant until all of the solder has melted. Once all of the solder has melted, continued heating would increase the temperature of the solder beyond its melting temperature to the temperature of the heater. Thus, when the temperature of the solder begins to rise, indicating complete liquefaction, the electrical current is shut off and a pump supplying propylene glycol to the capillary at a fixed mass flow rate is started. Time, temperature of the solder, and aerosol quality as visually observed, are monitored. Results may be found in Tables 1 and 2.

TABLE 1

| | | Solder | | |
|---|---|---|---|---|
| Example | Composition | Melting Point (° C.) | Heat of Fusion (J/g) | Mass (g) |
| 2 | 98% tin, 2% silver | 221 | 55 | 4.752 |
| 3 | 98% tin, 2% silver | 221 | 55 | 4.752 |
| 4 | 97% tin, 2% copper, 0.8% silver, 0.2% antimony | 230 | 61 | 3.858 |
| 5 | 97% tin, 2% copper, 0.8% silver, 0.2% antimony | 230 | 61 | 3.858 |

TABLE 2

| Example | Propylene Glycol Mass Flow Rate (mg/s) | Time (s) | Propylene Glycol Volatilized (mg) | Energy Required for Volatilization* (J) |
|---|---|---|---|---|
| 2 | 0.86 | 113 | 97 | 117 |
| 3 | 1.72 | 94 | 162 | 194 |
| 4 | 1.72 | 131 | 225 | 270 |
| 5 | — | 171 | — | — |

*1.2 J are required to volatilize 1 mg of propylene glycol

In Example 4, the solder was heated well beyond its melting point. The energy theoretically available from the heat of fusion of the solder was about 235 J (61 J/g×3.858 g). However, the energy required for volatilization of the propylene glycol for the observed 131 seconds was in excess of 235 J, and more specifically, 270 J. Thus, the observed 131 seconds during which propylene glycol was volatilized was longer than expected (i.e., 235 J/1.2 J/mg/1.72 mg/s=114 s). Without wishing to be bound by any theory, as it is believed that all of the propylene glycol was volatilized during that time period, it is further believed that the energy available from the solder exceeded its heat of fusion of 61 J/g. Assuming no energy loss in Example 4, the solder would have had to provide 70 J/g (270 J/3.858 g) in order to volatilize all of the propylene glycol; thus, the solder likely provided greater than 70 J/g. Accordingly, the listed values for heat of fusion provide a minimum value for energy provided by the solder. Heating of the solder beyond its melting point may result in poor aerosol formation, which may be identified by visual observation or an odor resulting from the breakdown of propylene glycol.

Example 5, with no propylene glycol flow (i.e., no liquid was supplied to the capillary), was made to determine power loss, i.e., power not transferred to propylene glycol, using a given mass of a known solder in the above-described tubular housing configuration. The solder was heated and when the temperature of the solder reached its melting point, the temperature of the solder remained fairly constant until all of the solder had melted. When the temperature of the solder began to rise, indicating complete liquefaction, the electrical current was shut off and a timer was started. As the electrical current was shut off when the temperature of the solder began to rise, the solder should not have been heated beyond its melting point, and the energy available from the solder would be equal to 61 J/g, its heat of fusion. The timer was stopped when the solder again reached a temperature equal to its melting point. Thus, a power loss of 1.4 W can be calculated for Example 5. Accordingly, a theoretical power requirement may be calculated by adding the calculated power loss to a calculated power requirement to volatilize a given mass of propylene glycol using the same mass of a known solder in the same tubular housing configuration.

While the preceding Examples disclose forming aerosol from propylene glycol, the use of a heat capacitor as a component of a capillary aerosol generator is not limited thereto, and may be useful in a variety of aerosol delivery applications, for, as noted above, its use enables operation of a capillary aerosol generator remote from a large energy source. For example, the heat capacitor may be useful for inhaler applications, e.g., drug delivery. Additionally, the heat capacitor may be used to generate flavored aerosols, which may, for example, be used to simulate a smoking experience.

While various embodiments have been described, it is to be understood that variations and modifications may be resorted to as will be apparent to those skilled in the art. Such variations and modifications are to be considered within the purview and scope of the claims appended hereto.

What is claimed is:

1. A component of a capillary aerosol generator comprising a heat capacitor, wherein the heat capacitor comprises a phase change material that changes phases at a temperature approximately equal to a temperature sufficient to volatilize liquid material in a capillary passage of the capillary aerosol generator.

2. The component of claim 1, wherein the phase change material comprises solder, the solder comprising one or more metals selected from the group consisting of tin, silver, antimony, bismuth, copper, and combinations thereof.

3. The component of claim 2, wherein the solder comprises a 98% tin-2% silver alloy.

4. The component of claim 1, wherein the phase change material surrounds the capillary passage.

5. The component of claim 1, wherein the phase change material is contained within a tubular-like housing.

6. The component of claim 5, wherein the tubular housing is wrapped with heating wire, which has electrical leads connected to it.

7. A capillary aerosol generator comprising:
a capillary passage adapted to form an aerosol when liquid material in the passage is heated to volatilize at least some of the liquid material therein; and
a heat capacitor comprising a phase change material in thermal contact with the capillary passage;
wherein the phase change material changes phases at a temperature approximately equal to a temperature sufficient to volatilize liquid material in the capillary passage.

8. The capillary aerosol generator of claim 7, wherein the phase change material comprises solder, the solder comprising one or more metals selected from the group consisting of tin, silver, antimony, bismuth, copper, and combinations thereof.

9. The capillary aerosol generator of claim 7, wherein the phase change material changes from a solid phase to a liquid phase; surrounds at least a portion of the capillary passage; and is contained within a tubular housing, the tubular housing being wrapped with heating wire, which has electrical leads soldered to it.

10. A method for generating aerosol using a capillary aerosol generator comprising the heat capacitor of claim 1, the method comprising:
supplying sufficient energy to the phase change material to cause the phase change material to change phases from a first phase to a second phase; and
supplying liquid material to the capillary passage;
wherein the phase change material supplies sufficient heat to the liquid material in the capillary passage, to volatilize liquid material in the capillary passage;
wherein volatilized liquid material is driven out of the capillary passage and mixes with ambient air to form aerosol.

11. The method of claim 10, wherein supplying energy to the phase change material comprises heating a tubular housing that contains the phase change material.

12. The method of claim 10, wherein the phase change material changes from a solid phase to a liquid phase.

13. The method of claim 12, wherein the liquid phase transfers heat to the capillary passage.

14. The method of claim 12, wherein the liquid phase is at a temperature sufficient to volatilize liquid material in the capillary passage.

15. The method of claim 12, wherein the liquid phase maintains a temperature sufficient to volatilize liquid material in the capillary passage for greater than about 10 seconds without active heating of the liquid phase.

16. The method of claim 15, wherein the liquid phase maintains a temperature sufficient to volatilize liquid material in the capillary passage for at least about 1 minute without active heating of the liquid phase.

17. The method of claim 10, further comprising supplying supplemental energy to the phase change material.

18. The method of claim 17, wherein supplying supplemental energy to the phase change material maintains the liquid phase.

19. The method of claim 10, further comprising monitoring the temperature of the phase change material with a thermocouple.

* * * * *